United States Patent [19]
Neyer

[11] Patent Number: 5,725,774
[45] Date of Patent: Mar. 10, 1998

[54] WHOLE BLOOD SEPARATION METHOD AND DEVICES USING THE SAME

[75] Inventor: Gebhard Neyer, Los Angeles, Calif.

[73] Assignee: LXN Corp., San Diego, Calif.

[21] Appl. No.: 418,523

[22] Filed: Apr. 7, 1995

[51] Int. Cl.$^6$ .......................... B01D 37/00; B01D 39/00; G01N 33/48; G01N 33/50
[52] U.S. Cl. .......................... 210/645; 210/483; 210/488; 210/489; 210/490; 210/496; 210/503; 210/504; 210/505; 210/506; 210/508; 210/767; 422/55; 422/56; 422/57; 422/60; 422/73; 422/101; 422/102; 422/169; 422/170; 422/177; 422/178; 530/412; 530/415
[58] Field of Search .......................... 210/483, 488, 210/489, 490, 496, 503, 504, 505, 506, 508, 767, 645, 650, 651, 806; 422/55, 56, 57, 60, 73, 101, 102; 436/16, 69, 169, 170, 177, 178; 530/412, 415

[56] References Cited

U.S. PATENT DOCUMENTS

| | | |
|---|---|---|
| 3,552,925 | 1/1971 | Fetter. |
| 3,552,928 | 1/1971 | Fetter. |
| 3,902,964 | 9/1975 | Greenspan .................. 436/177 |
| 4,256,693 | 3/1981 | Kondo et al. .................. 422/56 |
| 4,477,575 | 10/1984 | Vogel et al. .................. 436/170 |
| 4,543,338 | 9/1985 | Chen .................. 436/170 |
| 4,678,757 | 7/1987 | Rapkin et al. .................. 436/170 |
| 4,933,092 | 6/1990 | Aunet et al. .................. 210/729 |
| 5,064,541 | 11/1991 | Jeng et al. .................. 210/767 |
| 5,084,173 | 1/1992 | Nitadori et al. .................. 210/490 |
| 5,166,051 | 11/1992 | Killeen et al. .................. 422/55 |
| 5,169,757 | 12/1992 | Yamazaki et al. .................. 435/180 |
| 5,169,787 | 12/1992 | Knappe et al. .................. 436/169 |
| 5,186,843 | 2/1993 | Baumgardner et al. .................. 210/767 |
| 5,212,060 | 5/1993 | Maddox .................. 422/56 |
| 5,306,623 | 4/1994 | Kiser et al. .................. 422/57 |
| 5,366,868 | 11/1994 | Sakamoto .................. 435/10 |
| 5,397,479 | 3/1995 | Kass et al. .................. 210/782 |
| 5,423,989 | 6/1995 | Allen et al. .................. 210/650 |
| 5,470,752 | 11/1995 | Burd et al. .................. 436/87 |

FOREIGN PATENT DOCUMENTS

| | | |
|---|---|---|
| 2104976 | 3/1994 | Canada . |
| 0 194 502 | 9/1986 | European Pat. Off. . |
| 0 436 897 | 7/1991 | European Pat. Off. . |

OTHER PUBLICATIONS

Dialog Database Abstract of EPA 0 194 502 to Limbach and Helger, EPA published Sep. 17, 1986.

*Primary Examiner*—John Kim
*Attorney, Agent, or Firm*—Campbell & Flores LLP

[57] ABSTRACT

The present invention relates to a method and to a device for separating plasma from whole blood. The method and device utilize a permeable non-glass fiber matrix containing a polyol which is capable of clumping red blood cells. The matrix, in the absence of such a polyol, would otherwise be porous to red blood cells. The polyol-containing matrix has a first surface and a second surface such that a whole blood sample which is applied to the first surface flows directionally toward the second surface. Plasma separated from whole blood becomes available at the second surface of the matrix and can be tested for the presence of a particular analyte, such as glucose or fructosamine, as provided by multi-layer test devices of the present invention.

30 Claims, 1 Drawing Sheet

WHOLE BLOOD SEPARATION METHOD AND DEVICES USING THE SAME

FIELD OF THE INVENTION

The present invention relates generally to the chemical analysis of analytes present in whole blood and more specifically, to a method and to a device for separating plasma or serum from whole blood, thus providing a convenient and accurate means for such chemical analysis.

BACKGROUND INFORMATION

Presently, numerous test devices are available for the analysis of body fluids in order to determine the presence or concentration of a particular analyte. For example, tests are available for detecting glucose, fructosamine, albumin, calcium, urea, uric acid, bilirubin, cholesterol, and other soluble analytes present in whole blood or the fluid part of blood, namely the plasma or serum, after whole blood has been separated.

Many of these test devices utilize chromogenic or other visual responses to indicate the presence or absence, or the concentration, of an analyte being detected. Cellular components of whole blood, and in particular the red blood cells, have a deep red color which substantially interferes with chromogenic or other visual tests. Therefore, the highly-colored red blood cells as well as other interfering substances present in blood including hemoglobin and white blood cells are separated from the plasma or serum before a blood sample is assayed for a particular analyte.

Conventionally, the plasma or serum is separated from the cellular material of whole blood by centrifugation. The cellular material collects at the bottom of the centrifuge tube and the supernatant plasma or serum is decanted and tested for a particular analyte. Centrifugation, however, is time consuming, involves extra manipulative steps and requires equipment that is generally not present outside of the clinical laboratory. Thus, reliance on centrifugation makes field testing, such as testing at the doctor's office or at the patient's home, difficult.

Certain methods other than centrifugation have been developed to separate the cellular components of whole blood from plasma or serum. Some of the earlier methods, such as that described in U.S. Pat. No. 4,543,338 to Chen, involve the use of a carrier membrane impregnated with a test reagent and coated with a semipermeable membrane. The semipermeable membrane effectively acts as a means for filtering out cells or large molecules, such as hemoglobin, but allows the passage of smaller molecules and ions which then contact the testing reagents impregnated in the bibulous matrix. These methods, however, typically require an extra manipulative step, such as rinsing with water or wiping off the test device so as to remove cellular material retained on the semipermeable membrane. Such techniques can be cumbersome and laborious. Moreover, if the red blood cells are not completely removed or rinsed from the semipermeable barrier, interference with the assay remains a problem.

Another method for separating whole blood is described in U.S. Pat. No. 4,477,575 to Vogel et al. which describes separating plasma or serum from whole blood using a layer of glass fibers having a defined average diameter and density. As well, Baumgardner et al. in U.S. Pat. No. 5,186,843 describe the use of glass fibers in a single separation layer. Blood separation devices utilizing glass fiber filters, however, tend to separate serum at a relatively slow speed and tend to retain significant quantities of serum or plasma in the interstices of the glass fiber matrix.

Alternative approaches to blood separation involve incorporating agglutinating reagents or other separation reagents in a matrix. For example, Aunet et al. in U.S. Pat. No. 4,933,092, Daubney et al. in published Canadian Patent Application No. 2,104,976, and Limbach in European Patent Application 0 194 502 all describe the use of polymeric agglutinating agents, such as cationic polymers, which, for example, in Daubney and in Limbach are combined with additional agglutinating agents, such as lectins. As well, Barkes et al. in European Patent Application No. 0 436 897, describe the use of lectins and thrombin incorporated into a suitable carrier matrix. However, such matrices incorporated with these types of agglutinating agents exhibit problems similar to those associated with glass fiber matrices. For example, the separation may occur at a relatively slow speed and the amount of plasma or serum separated may be limited to 50% of the absorption volume of the matrix, often requiring the use of external pressure, such as in European Patent Application 0 194 502, in order to obtain the maximum efficiency and quantity of plasma or serum.

Other separating agents, such as water-soluble salts, amino acids, carbohydrates and large polymers, such as polyethylene glycol, polyvinyl alcohol and the like, have been incorporated into single matrix test strips. Fetter in U.S. Pat. Nos. 3,552,925 and 3,552,928 describes a test device having a bibulous matrix impregnated with an inorganic salt or amino acid at a first region on the matrix and test reagents impregnated at an adjacent second region. While the salts or amino acids used in this process can separate the cellular components from the whole blood, they also introduce contaminating ions or molecules into the plasma or serum and precipitate a portion of the soluble plasma or serum constituents, thus rendering a quantitative assay for the soluble constituent unreliable. Rapkin et al. in U.S. Pat. No. 4,678,757 describe the use of carbohydrates, such as mannitol, impregnated or coated onto a carrier, preferably coated onto an impermeable carrier. The described device, whether having a permeable or impermeable carrier, however, only provides for capillary and longitudinal transport of the blood. Therefore, the blood separation matrices of Rapkin et al. are not described as being useful in test devices that operate primarily by gravitational force, as do many of the multi-layer test devices currently used by doctors or patients. While Kiser et al. in U.S. Pat. No. 5,306,623 describe separation matrices which can operate by wicking gravity flow, Kiser et al. use large polymeric separating reagents, such as polyethylene glycol, polystyrene sulfonic acid, hydroxypropyl cellulose, polyvinyl alcohol, polyvinylpyrrolidone, and polyacrylic acid. Upon application of a whole blood sample, such large polymers contained within a matrix would be solubilized, potentially blocking the pores of the matrix and most certainly rendering the sample more viscous, thereby slowing the separation process and decreasing the yield of plasma.

Based on the shortcomings of these methods, there exists a need for a device that provides rapid and efficient methods for the separation of plasma or serum from whole blood. In particular, there is an increasing awareness of the importance of, and accordingly a need for, being able to carry out diagnostic assays at the doctor's office or, better yet, at home. Therefore, there exists a need to minimize any extra manipulative steps, such as the rinsing or wiping of test devices or the application of external pressure. Moreover, there is a need for rapid separation which is reliable and does not contain interfering substances. The present invention satisfies these needs and provides related advantages as well.

SUMMARY OF THE INVENTION

The present invention relates to a method and to a device for separating plasma from whole blood. The method and device utilize a permeable non-glass fiber matrix containing a polyol which is capable of clumping red blood cells. The matrix, in the absence of such a polyol, would otherwise be porous to red blood cells. The polyol-containing matrix has a first surface and a second surface such that a whole blood sample which is applied to the first surface flows directionally toward the second surface. Plasma separated from whole blood becomes available at the second surface of the matrix and can be tested for the presence of a particular analyte, such as glucose or fructosamine, as provided by multi-layer test devices of the present invention.

DETAILED DESCRIPTION OF THE INVENTION

Figure 1:
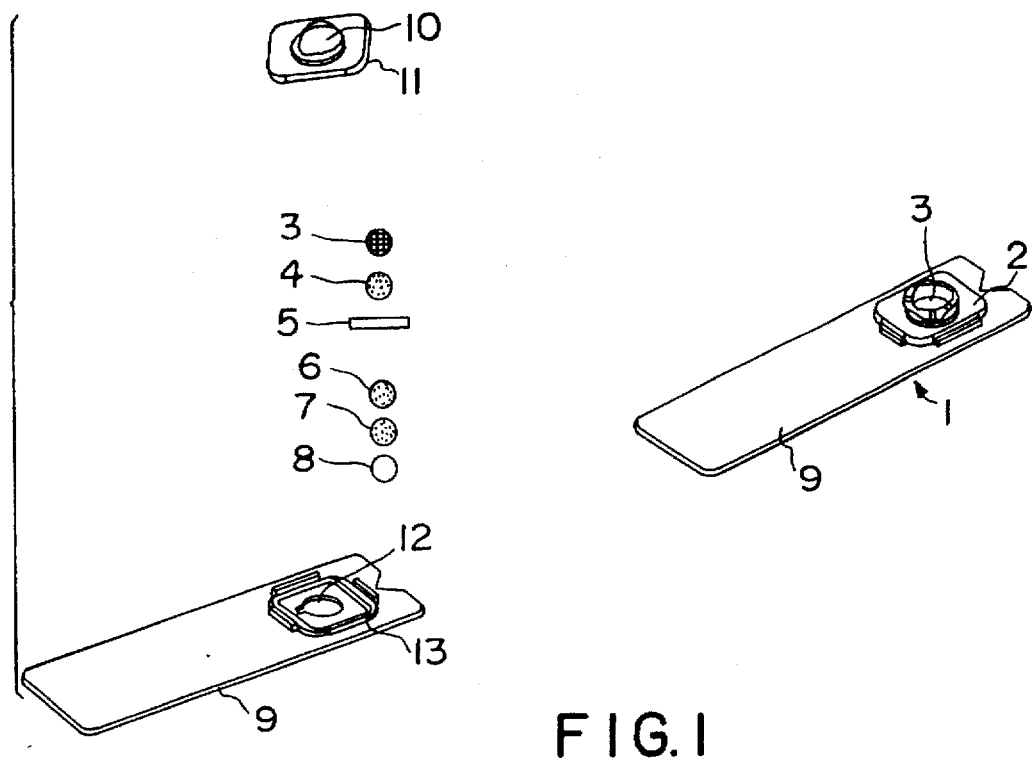
FIG. 1 depicts one embodiment of a multi-layer fructosamine test device which can be used for separating plasma from a whole blood sample and measuring the concentration of fructosamine.

There is an increasing awareness of the importance of being able to carry out diagnostic assays at the doctor's office or, better yet, at home. For example, a diabetic's blood glucose level fluctuates significantly throughout a given day, being influenced by diet, activity, and treatment. Depending on the nature and severity of the individual case, some diabetic patients measure their blood glucose levels up to seven times a day. Clearly, the results of these tests should be available to the patient immediately.

Because of the frequent fluctuation of glucose levels in a given day, tests which are independent of a patient's diet, activity, and/or treatment and which provide longer term indications of blood glucose levels have been developed. These tests measure the concentration of glycated proteins or "frucosamines." Proteins, such as those present in whole blood, plasma, serum and other biological fluids react with glucose, under non-enzymatic conditions, to produce glycated proteins. The extent of the reaction is directly dependent upon the glucose concentration of the blood. Measurement of serum or plasma fructosamine levels is useful for monitoring diabetic control because fructosamine concentrations in serum or plasma reflect an average of blood glucose level over approximately a half month period.

Scandinavian investigators recently showed that doctors and patients who were made aware of their glycated protein test results had better glycemic control than those who were unaware of such results. Moreover, it is now believed that glycated proteins can be the causative agents of complications associated with diabetes, which include retinopathy, nephropathy, neuropathy and cardiovascular disease. Therefore, any delay in information transfer, such as a doctor's delay in reporting clinical test results to a patient, decreases the value of the test result. Again, this emphasizes the importance in being able to perform diagnostic assays at the doctor's office or at home.

For an assay to be useful in the doctor's office or home, the test should be relatively free of sensitivity to small changes in the conditions under which the assay is carried out and the measurements should be accurate and reliable. Equally as important, if not more so, the assay must have a simple and convenient protocol which does not involve extra manipulative steps. To enhance the simplicity and convenience of such tests, the preferable body fluid for testing such analytes as glucose and fructosamine is whole blood which can simply be taken from a finger or earlobe puncture. Such simple and rapid determinations of an analyte in blood is especially desirable in the case of an emergency.

As described above, the simplicity and accuracy of such tests depends to a large extent on the whole blood separation layer contained within the test device and the ability of the blood separation matrix to provide uncontaminated plasma or serum. The present invention provides a method and device, namely a blood separation matrix, which is capable of such simple and accurate blood separation. Of particular importance, the matrix contains a polyol which causes red blood cells contained in whole blood to clump. The clumped red blood cells either can be retained in the matrix or can be filtered by a filter material. The method and matrix can be used in various test devices which analyze whole blood for a particular analyte, such as, the fructosamine and glucose test devices provided by the present invention.

As used herein, the term "plasma" means the substantially colorless fluid obtained from a whole blood sample after red blood cells have been removed by the separation process and device of the present invention. Because plasma is serum plus the clotting protein fibrinogen, the term "plasma" is used broadly herein to include both plasma and serum.

In order to obtain plasma from whole blood, the present invention provides a permeable non-glass fiber matrix containing a polyol which is capable of clumping red blood cells. The matrix is porous to red blood cells in the absence of such a polyol. The matrix has a first surface for sample application and a second surface where plasma is received or becomes available. If desired, the matrix additionally can contain a polycationic polymer. Also useful, though not required, is a permeable filter material or membrane supporting the separation matrix which serves as a final filter to red blood cells and/or provides a reagent layer for effecting an assay. Each of these components of the invention, as well as test devices which use the blood separation method and matrix of the present invention are disclosed in detail.

MATRIX

The separation matrix of the present invention is a permeable matrix which does not contain glass fibers and, therefore, is termed "a permeable non-glass fiber matrix." The term "permeable" means liquid-permeable, such as permeable to plasma, as well as permeable or porous to red blood cells when the matrix is provided in the absence of a polyol. As used herein, the phrase "matrix being porous to red blood cells in the absence of a polyol" means that without the polyol contained in or on the matrix the red blood cells would simply pass through the matrix, virtually immediately. In the absence of the polyol, red blood cells are not retained, by filtration or otherwise, in the matrix.

The polyol contained within or on the matrix chemically reacts with the whole blood sample so as to clump the red blood cells. As used herein, "clump" or "clumping" means the collection into a mass or group, red blood cells distributed in a whole blood sample. While not wishing to be bound by any theory or mechanism, the clumping can be the result of agglutination, coagulation, or the like, or some other chemical interaction between the polyol and the red blood cells. Thus, the present invention is not strictly a filtration process, for example, based on the pore size of the matrix, as described, for example, in U.S. Pat. No. 4,543,338 to Chen, or as used in a glass fiber prefilter, such as that described in U.S. Pat. No. 4,477,575 to Vogel et al. Rather, it is the presence of a polyol which provides the matrix with its ability to separate plasma from whole blood by clumping the red blood cells.

Surprisingly, the clumping of the red blood cells by the polyol does not substantially block the flow of the whole blood sample or plasma through the matrix. Thus, sufficient amounts of plasma become available at the second surface of the matrix. Sufficient quantities of plasma can rapidly be obtained for the specific applications exemplified herein, namely analyzing the concentration of frucotosamine or glucose in drops of whole blood. The present invention can be used with other applications and diagnostic assays as well, including ones which use a larger volume of blood or which require more plasma. With as small as a $\frac{3}{16}$" diameter circle of a polyol-containing matrix of the present invention, as much as 10 µl of plasma can be obtained from a drop of blood. Therefore, a matrix of the present invention can be used for separating larger volumes of blood than a drop of blood. Accordingly, the matrix can be used in diagnostic applications which analyze larger quantities of blood, such as for example, some known cholesterol tests.

A useful permeable matrix can be a woven or non-woven material and can be an absorbent or a non-absorbent material which may or may not be hydrophilic. Especially suitable materials for the matrix include, for example, woven or non-woven, absorbent or non-absorbent, nylon, rayon, cotton, and polyester. In one embodiment of the invention, the matrix is a non-woven, non-absorbent polyester. The polyester is preferably a poly(paraphenylene terephthalate), such as that used in a preferred polyester sold as Sontara® (DuPont, Inc., Wilmington, Del.). Another preferred matrix is the woven, absorbent nylon Tetex® 3-3710 (Tetko, Inc., Lancaster, N.Y.).

Depending upon the porosity or other properties of the matrix, the clumped red blood cells either are retained in the matrix or are filtered out by the filter material as described below. Some of the above-described matrix materials, such as the non-woven, non-absorbent polyesters, do not have "pores" in the traditional sense, i.e., that can be measured, for example, by pore size (microns). In the absence of a polyol of the present invention such materials essentially have no limit as the porosity and are porous to red blood cells, which have an average size of 5 µm. With such macroporous materials, if the polyol is not present the red blood cells pass through the matrix almost immediately. For those matrix materials which can be characterized based on pore size, the matrices used in the present invention can have a pore size generally of from about 2 µm to about 10 µm. Such pores sizes can be useful for retaining the clumped red blood cells. Depending upon the porosity, thickness, which is generally 200 to 1100 µm, and other properties of the matrix, such as absorbency, the clumped red blood cells are either retained in the matrix or captured in a final filter material as described below.

The polyol-containing matrix has a first surface for sample application and a second surface where plasma is received or becomes available for testing or additional separation. Generally, the first and second surfaces are presented as opposite sides of the matrix. The whole blood sample flows in a direction from the first surface toward the second surface, under conditions which provide such directional flow, such as, gravitation, vacuum, or external pressure. To enhance the simplicity of the method, if desired, separation can be performed by gravity alone. Preferably, the separation matrix provides for flow in a vertical direction, preferably by gravitation.

Rapkin et al. in U.S. Pat. No. 4,678,757, describe the use of carbohydrates, such as mannitol, impregnated or coated onto a carrier, preferably coated onto an impermeable carrier. However, the described device of Rapkin et al., whether having a permeable or impermeable carrier, only provides for capillary and lateral transport of the blood. There can be divergent contact times provided by vertical flow, a relatively short period of contact, versus lateral flow, a slow process which can involve continuous interaction between a whole blood sample and a matrix. Because of these variable contact times, it is not predictable that what works by lateral flow would similarly work under vertical flow. Unexpectedly, with the present invention, even with matrices which are porous to red blood cells in the absence of a polyol, a matrix containing a polyol can effectively separate plasma from whole blood even when the blood sample flows vertically through the matrix.

POLYOL

The separation method and device include a permeable non-glass fiber matrix containing a polyol. As used herein, the terms "matrix containing a polyol" and "polyol-containing matrix" mean that the polyol is separately added to the matrix and is not a component originally found in the composition or make up of the matrix, such as cellulose filter paper. Further, "matrix containing a polyol" means a polyol can be impregnated into the matrix or coated into or onto the matrix or covalently or non-covalently bound to the matrix. In a preferred embodiment, the polyol is impregnated into the matrix.

As used herein, the term "polyol" means a polyhydroxy alcohol which is an alkyl or aromatic containing more than one hydroxyl group. The term "poly" as used in "polyol" does not infer that the alkyl or aromatic compound is a large polymer made up of repeating monomeric units, but, instead, means that more than one hydroxyl group is present in the compound. As discussed more fully below, with the exception of polysaccharides, the polyols used in the present invention are simple sugars or sugar alcohols, oligosaccharides, or other naturally or non-naturally occurring non-polymeric alkyl or aromatic compounds. Therefore, the term "polyol" encompasses sugars, alcohol derivatives of sugars, herein termed "sugar alcohols," and other naturally or non-naturally occurring non-polymeric polyols.

As used herein, "sugar" includes monosaccharides, oligosaccharides, and polysaccharides. A monosaccharide is a simple sugar which is as a linear, branched, or cyclic polyhydroxy alcohol containing either an aldehyde or a ketone group. Exemplary monosaccharides include, but are not limited to, mannose, glucose, talose, galactose, xylose, arabinose, lyxose, ribose and fructose. An oligosaccharide is a linear or branched carbohydrate that consists from two to ten monosaccharide units joined by means of glycosidic bonds. Oligosaccharides which can be used in the present invention include, but are not limited to disaccharides such as sucrose, trehalose, lactose and maltose. Examples of larger oligosaccharides which can be used in the invention include the cyclodextrins, such as alpha-cyclohexylamylose, beta-cycloheptaamylose, and gamma-cyclooctoamylose, as well as other oligosaccharides well known in the art. A polysaccharide is any linear or branched polymer having more than ten monosaccharides linked together by glycosidic bonds. Exemplary polysaccharides include, but are not limited to, ficoll, polysucrose, and hydroxyethyl starch.

Encompassed within "sugar" are those sugars which are naturally occurring as well as those which are known but which have not yet been identified as occurring naturally in plants or animals. For example, there are five known naturally occurring aldohexoses, including D-glucose, D-mannose, D-talose, D-galactose, and L-galactose. However, the aldohexose structure has four chiral carbons and thus, sixteen possible stereoisomers, all of which are known, although only the five listed above have been identified as occurring naturally in plants or animals. Thus, "sugar" encompasses enantiomers in either the D or L forms of a sugar as well as racemic mixtures thereof.

A polyol of the present invention also can be a "sugar alcohol." A "sugar alcohol" is an alcohol derivative of a mono- or an oligosaccharide which is generally formed by reduction of the aldehyde or ketone moiety on the mono- or oligosaccharide. Exemplary sugar alcohols include, but are not limited to, mannitol, sorbitol, arabitol, inositol, galactitol, erythritol, and threitol. Also included within the definition of "sugar alcohol" are the alcohol derivatives of those mono- and oligosaccharides described above.

Where chiral carbons are present in the sugar alcohol, the sugar alcohol may be in the D or L form, such as D-threitol or L-threitol, or in a racemic mixture of both the D and L forms. The sugar alcohol can, but does not have to, be naturally occurring. That is, the sugar alcohol can be a derivative of a known, naturally occurring sugar, or, alternatively, it can have a D or L configuration known to exist but not necessarily identified as occurring in nature. The sugar alcohol also can be a sugar which is found naturally in its reduced alcohol form or it can be an alcohol derivative of a sugar which derivative is not known to exist in nature.

In addition to sugar or sugar alcohols, the polyol can be a non-polymeric naturally occurring or non-naturally occurring polyol, which includes linear, branched, or cyclic alkyl or aromatic compounds containing more than one hydroxyl group. As used herein the term "non-polymeric" means the alkyl or aromatic compounds are not polymers. Polymers are defined as high molecular weight compounds consisting of long chains that may be open, closed, linear, branched, or crosslinked, which chains are composed of repeating units, called monomers, which may be either identical or different. As used herein, those polyols which are "naturally occurring" are ones which occur in nature and those which are "non-naturally occurring" are not found in nature. Generally, these naturally occurring or non-naturally occurring alkyl or aromatic compounds range in size from three to twenty carbons ($C_3$ to $C_{20}$), and more preferably, from three to ten carbons ($C_3$ to $C_{10}$). Examples of such naturally occurring, non-polymeric polyols are glycerol, a three-carbon trihydroxy alcohol that occurs in many lipids, and quinic acid, a 1,3,4,5-Tetrahydroxycyclohexanecarboxylic acid, which acid can be in the salt form. Examples of non-naturally occurring, non-polymeric polyols include pentaerythritol and dipentaerythritol.

Kiser et al. in U.S. Pat. No. 5,306,623 describe the use of large polymeric separating reagents, such as polyethylene glycol, polystyrene sulfonic acid, hydroxypropyl cellulose, polyvinyl alcohol, polyvinylpyrrolidone, and polyacrylic acid. Upon application of a whole blood sample, such large polymers contained within a matrix would be solubilized, potentially blocking the pores of the matrix and most certainly rendering the sample more viscous, thereby slowing the separation process and decreasing the yield of plasma. Therefore, with the exception of the above-described polysaccharides, the invention does not involve the use of large alkyl polymers as the primary separating agent. The matrix described in U.S. Pat. No. 5,306,623 is different from the instant invention in a number of other aspects as well. For instance, the Examples given in U.S. Pat. No. 5,306,623 involve the use of matrices which have a very small pore size, less than 1 µm, which would act as a filter to red blood cells in the absence of the disclosed polymers. As discussed above, the present invention is not strictly a filtration process, rather it involves the use of polyols which clump red blood cells and in the absence of such polyols the matrix would be porous to red blood cells. Moreover, the matrices taught by Kiser et al., in addition to a polymer, also contain the test reagents, which reagents may substantially influence the separation and test results. The separation matrix of the present invention does not contain the test reagents. The test reagents, as disclosed in greater detail below, are either on the filter material or additional test reagent layers and the like.

In one embodiment, to apply the polyol to the matrix, the polyol can simply be dissolved in an aqueous solution generally, at a concentration of about 20% when used alone, and at about 10% concentration when combined with a polycationic polymer, which is generally present in a concentration of about 0.5% to 5% as discussed more fully below. If desired, multiple layers of matrices containing polyol at lower concentrations, such as four layers of matrix containing 5% polyol, also can be used. The polyol and, if present, the polycationic polymer can alternatively be dissolved in physiological saline (0.85% NaCl), phosphate buffered saline (PBS), an organic solvent, or the like.

POLYCATIONIC POLYMER

In addition to the polyol, a polycationic polymer can, but does not have to, be added to the matrix. Similar to the addition of a polyol to the matrix, the polycationic polymer can also be physically impregnated, coated into or onto, or covalently or non-covalently bound to the matrix. The polycationic polymer is also useful for clumping, as well as stabilizing clumped, red blood cells, the latter of which is described for example, in the published Canadian Patent Application No. 2,104,976 to Daubney et al., which is incorporated herein by reference.

The polycationic polymer component can be any polymer having more than one cationic site and are generally based on monomers which contain an amine group. Suitable polycationic polymers include, for example, hexadimethrine bromide, trimethylenehexamethylenediammoniumbromide, polylysine, polyallylamine, polyarginine, poly(N,N-dimethylaminoethylmethacrylate, copolymers of N,N-dimethylaminoethylmethacrylate and methylmethacrylate, polyethyleneimine, poly(diallyldimethylammonium chloride), poly(1,1-dimethyl-3,5-dimethylenepiperidinium chloride), and mixtures thereof. The polymerized positively charged amino acids, such as polylysine, can have the amino acids in either the D or L forms, such as poly-L-lysine or poly-D-lysine, or a racemic mixture thereof, such as poly-D,L-lysine.

As described above, in one embodiment, to apply the cationic polymer to the matrix, the polymer can be dissolved in an a solution such as water, physiological saline, PBS, an organic solvent, or the like, and the matrix then dipped into the polymer containing solution. Generally, the polymer is in a concentration of about 0.5% to 5%. Where both polyol and polymer are contained in the matrix, the order of adding polyol and polymer to the matrix is irrelevant. For example, polyol and polymer can be simultaneously or sequentially dissolved in such aqueous solutions or solvents as those described above and both polyol and polymer simultaneously applied to the matrix, as described in the Examples below. Alternatively, polyol and polymer can be applied to the matrix sequentially in any order.

Non-hemolytic detergents, such as Pluronic (Pragmatics, Inc., Elkhart, Ind.), can be added to the aqueous solutions or solvents described above, generally at a concentration of 0.01% to 0.1%. Such detergents help maximize impregnation of a polyol into the matrix, thereby improving the flow rate of the whole blood sample and the plasma. Other optional agents which can further enhance the flow rate, include, for example, polyvinylpyrrolidone or similar polymers and other fillers which give the matrix and the below described filter material stiffness.

FILTER

Though not required, a filter material can be used in combination with the matrix of the present invention. Suitable filter materials include, for example, nylon, cellulose acetate, polysulfone, synthetic fibers, and polycarbonate. The filter can, but does not have to, be a membrane. Illustrative filters and membranes include, for example, BTS polysulfone membrane (Memtek, Inc., San Diego, Calif.), Ahlstrom synthetic fiber sheets, such as 94-30 A (Ahlstrom Filtration, Inc., Mt. Holly Spring, Pa.), Biodyne A® nylon membrane (Pall Corp., East Hills, N.Y.), Ultrabind 450 (Gelman, Ann Arbor, Mich.), and Nucleopore® polycarbonate (Costar, Corp., Cambridge, Mass.).

The need for any additional filter material depends to a large extent on the porosity, thickness, absorbency or other properties of the matrix. For example, the clumped red blood cells, depending upon the above properties of the matrix, can be retained in the matrix. Alternatively, or in addition thereto, a final filter material can be used to capture or retain any additional clumps of red blood cells. Where present, the filter material can generally have a porosity of up to about 12 μm and preferably will have a pore size of less than 10 μm, and more preferably 5 μm or less.

A filter material can be placed underneath the polyol-containing separation matrix, thereby supporting the matrix. Because the filter or membrane is at the second surface of the matrix where the plasma becomes available, the filter material can also serve as a reagent layer. The filter material can contain at least one chemical reagent for determining the presence of an analyte in the plasma. Determining the presence of an analyte can be a qualitative or quantitative determination.

In preferred embodiments of the invention, the blood separation method and device comprise a non-woven, non-absorbent polyester matrix impregnated with mannitol and either a nylon or polysulfone membrane below the matrix. Preferably, the matrix additionally contains hexadimethrine bromide. The membrane can additionally contain at least one chemical reagent for analyzing the concentration of an analyte such as glucose present in a whole blood sample.

Figure 2:
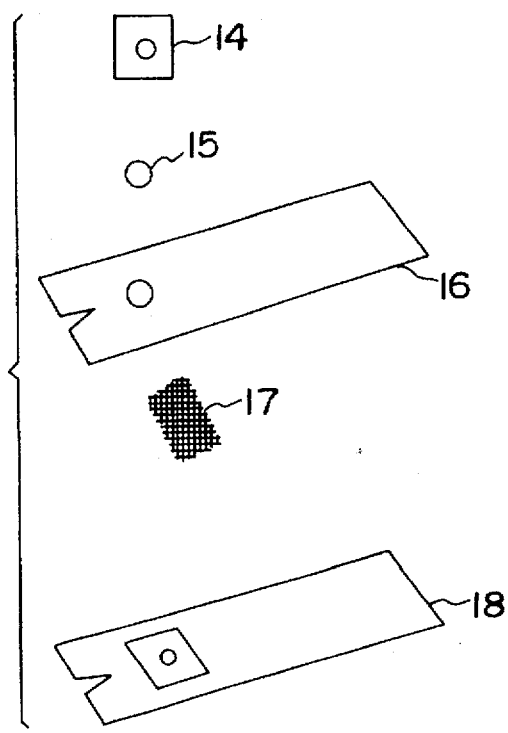
FIG. 2 exemplifies one embodiment of a glucose test device which is useful for separating plasma from whole blood and measuring the concentration of glucose.

In one embodiment of the invention, provided in FIG. 2 and Example 2, the filter membrane contains test reagents for determining glucose concentration in whole blood. Referring to FIG. 2, the glucose test device of the present invention has a polyol-containing blood separation matrix 15 which can be held in position by a mask 14 and a plastic support member 16, below the latter of which is a membrane 17 containing glucose test reagents, held in position by a plastic support member 18.

Chemical reagents for determining the presence or absence or the concentration of various analytes, such as glucose or fructosamine, are well known in the art. For example, such test reagents which produce a signal in response to glucose typically involve a glucose oxidase enzyme reaction. Glucose and glucose oxidase enzyme react to produce hydrogen peroxide. A peroxidase, such as horse radish peroxidase, and a redox indicator, such as o-tolidine, o-dianisidine, 3,3,5,5-tetramethylbenzidine (TMB), 4-aminoantipyrine, and others well known in the art, can be oxidized in the presence of hydrogen peroxide to produce a colored product. Such reagents for determining glucose presence and concentration are disclosed, for example, in European Patent Application 0388782 to Chen, and U.S. Pat. No. 5,304,468 to Phillips et al., both of which are incorporated herein by reference.

As described above, though not required, the filter material can serve as a final filter in the blood separation process. In another embodiment, the filter is provided without the presence of chemical test reagents. For example, referring to an alternative embodiment of the invention, as shown in FIG. 1, a multi-layer fructosamine test device containing the blood separation matrix of the present invention in combination with a membrane can be used to determine the concentration of fructosamine present in whole blood. Referring now to FIG. 1, a fructosamine multi-layer test device 1 has a blood separation matrix 4 and membrane 5, below which is the reagent layers, including a buffer layer 6 and an indicator layer 7 as well as clear plastic window 8 for reading the test results on the indicator layer 7. A mesh layer 3, used to press the multi-layers together, and the separation matrix 4 are contained in a guard piece 11 and sealed with the membrane 5. Layers 6, 7, and 8 are contained in opening 12 of well 13 which is on plastic support member 9. Pieces 11 and 13 containing the respective layers are ultrasonically welded together 2.

Test reagents for determining the presence or concentration of fructosamine such as the appropriate buffers and indicator reagents, including chromogenic dyes, or fluorescent reagents, are known in the art, for example, as described in U.S. patent application Ser. No. 08/269,351, which is incorporated herein by reference.

The buffer layer 6 of the fructosamine test generally contains a buffer having a pH value of at least 9. Various known buffers can be contained in the buffer layer so long as the buffer provides sufficiently high pH such that the fructosamines are converted to their eneaminol form. The eneaminol form of fructosamine is a chemically active reducing substance that reacts with a suitable indicator capable of being reduced by fructosamine. To achieve this, the pH of the buffer should be at a pH value between about 9 and about 13 and, for optimum results, the pH is at a pH value of between 10 and 12. Examples of such buffers include potassium hydrogen phosphate, sodium hydrogen phosphate, sodium hydroxide, guanidinium salts, certain amino acids, and other suitable buffers as are well known in the art, or combinations thereof.

The indicator layer 7 of the fructosamine test device contains any indicator capable of being reduced by fructosamine such as certain dyes, including chromogenic dyes, or fluorescent reagents. Examples of suitable chromogenic dyes which change color based on the amount of fructosamine present in a liquid sample include tetrazolium dyes such as Neotetrazolium chloride (NT), Tetranitroblue tetrazolium chloride (TNBT), Blue tetrazolium chloride (BT), Iodonitrotetrazoilum chloride, Nitroblue tetrazolium chloride (NBT), Nitro blue monotetrazolium chloride, Thiazolyl blue tetrazolium bromide (MTT), Tetrazolium violet, 2,3,5-Triphenyl-2-H-tetrazolium chloride, Thiocarbamyl nitro blue tetrazolium chloride (TCNBT), Tetrazolium XTT (XTT), 2-2'-Benzothiazolyl-5-styryl-3-(4'- phthalhydrazidyl) tetrazolium chloride (BSPT), Distyryl nitroblue tetrazolium chloride (DSNBT). An example of a suitable fluorescent reagents is 5-Cyano-2,3-ditolyl tetrazolium chloride (CTC).

The following examples are intended to illustrate but not limit the invention.

EXAMPLE

Fructosamine Test

This Example provides the preparation and testing of a multi-layer fructosamine test device using a whole blood separation matrix of the present invention. Because the presence of red blood cells normally interferes substantially with the analysis of fructosamine in whole blood, this Example compares testing for fructosamine in a whole blood sample using the present invention versus testing for fructosamine in a serum sample.

A. Blood Separation Layer

Mesh: A Tetko mesh #7-280/44 (Tetko, Inc. Rueschlikon, Switzerland) was placed in a detergent solution of 1% Pluronic (Pragmatics, Inc.) for 1 minute. Excess detergent was removed and the mesh was dried by heating at 60° C. for 10 minutes. Mesh was stored in desiccated plastic bags until ready for use at which time a 3/16" circle of the mesh was placed in the fructosamine multi-layer test device.

Blood Separation Matrix: A solution of 10% mannitol and 1.25% hexadimethrine bromide in physiological saline (0.85% NaCl) was impregnated onto Sontara® #8007 (DuPont, Inc.) on an automated impregnation/drying unit (AFM Engineering, Santa Anna, Calif.). The drying temperature was 100° C. for approximately 10 minutes.

Membrane: An untreated BTS polysulfone membrane of 0.85 p/n pore size (Memtek, Inc.) was cut into a 3/16" for use as an additional filter below the blood separation matrix.

B. Reagent Layers:

Buffer Layer: A 1M solution of aqueous sodium phosphate (aqueous $NaH_2PO_4$) containing 1M guanidinium carbonate buffer was titrated with sodium hydroxide (NaOH) to yield a 100 ml solution at pH 11. After addition of 0.5% Surfactant 10G detergent (Pragmatics, Inc.) the mix was impregnated onto Whatman 540 paper and dried for 10 minutes at 100° C.

Dye Layer: A 10 mM methanolic solution of nitroblue tetrazolium chloride (NBT) containing 200 μM N-ethylmethoxyphenazine ethylsulfate and 1% Gantrez® AN 119 was impregnated onto Whatman 54 paper and dried for 15 minutes at 60° C.

The layers (3/16" circles) were assembled as follows:

Tetko Mesh (top)

Mannitol Containing Matrix

Polysulfone Membrane

Buffer Layer

Dye Layer (bottom)

The layers were held in place by an injection molded plastic part. Whole blood and serum (15 μl) from the same donor were applied at the top and reaction rates were measured at the bottom as follows:

| Sample | Starting K/S | ΔK/S (1 to 2 min.) |
| --- | --- | --- |
| whole blood | 0.214 | 0.184 |
| serum | 0.201 | 0.184 |

The results demonstrate that the reaction rate with the whole blood sample is the same as that with the serum sample. These results indicate that there was no interference from red blood cells and, therefore, that the whole blood separation of the present invention successfully removed the red blood cells present in the whole blood sample.

EXAMPLE II

Glucose Test

This Example demonstrates the preparation and testing of a rapid glucose test containing a blood separation matrix of the present invention. The Example tests for glucose in spiked whole blood samples.

A. Blood Separation Matrix:

A #8007 Sontara® impregnated with 10% mannitol and 1.25% hexadimethrine bromide was prepared as described above, except that the sugar alcohol and polymer were dissolved in water.

B. Filter Membrane and Chemical Reagent Layer: A sheet of 0.45 μm Biodyne A® nylon (Pall Corp.) was dipped into an aqueous solution containing the following reagents:

| | |
| --- | --- |
| 0.30 M | Citrate Buffer |
| 1.25% | Gelatin 150 Bloom |
| 1106 U/ml | Glucose Oxidase |
| 479 U/ml | Horseradish Peroxidase |
| 0.43% | 4-Aminoantipyrine (AAP) |
| 1.52% | N-ethyl-N-(2-hydroxyl-3-sulfopropyl)-m-toluidine Sodium Salt (TOOS) |
| 0.25% | Pluronic L64 (Poly(oxyethylene-co-oxypropylene) block polymer |
| 1% | Gantrez ® L139 |

After dipping, the sheet was dried for 20 minutes at 50° C. The blood separation matrix was mounted on top of the nylon membrane containing the test reagents and the two held together by adhesive. A drop each of four glucose spiked blood samples were applied to the first surface of the mannitol containing Sontara® matrix. The results are as follows:

| Glucose Level (mg/dl) | K/S (at 45 seconds) |
| --- | --- |
| 98 | 0.732 |
| 180 | 0.986 |
| 297 | 1.312 |
| 450 | 1.747 |

These results demonstrate that the color produced was proportional to the glucose concentration in the blood sample and that a linear dose/response curve was accurately obtained, indicating good performance.

Although the invention has been described with reference to the disclosed embodiments, those skilled in the art will readily appreciate that the specific examples detailed are only illustrative of the invention. It should be understood that various modifications can be made without departing from the spirit of the invention. Accordingly, the invention is limited only by the following claims.

We claim:

1. A process for separating plasma from a whole blood sample, comprising:

(a) applying the whole blood sample to a first surface of a permeable non-glass fiber matrix containing (1) a $C_3$ to $C_{20}$ polyhydroxy alcohol capable of clumping red blood cells and (2) a polycationic polymer, said matrix being porous to red blood cells in the absence of said polyhydroxy alcohol;

(b) flowing said whole blood sample under conditions which allow said sample to flow vertically toward a second surface of said matrix, said first and second surfaces being on opposite sides of said matrix; and (c) receiving plasma separated from said whole blood sample at said second surface.

2. The process of claim 1, wherein the polycationic polymer is hexadimethrine bromide.

3. The process of claim 1, wherein said matrix is supported by a permeable filter material.

4. The process of claim 3, wherein the permeable filter material is a reagent layer containing at least one chemical reagent for determining the presence of an analyte in the plasma.

5. The process of claim 4, wherein said chemical reagent provides a color determination.

6. The process of claim 4, wherein determining the presence of an analyte is a quantitative determination.

7. The process of claim 3, wherein the permeable filter material is selected from the group consisting of a nylon, a cellulose acetate, a polysulfone, a synthetic fiber, and a polycarbonate.

8. The process of claim 1, wherein the polyhydroxy alcohol is impregnated in the matrix.

9. The process of claim 1, wherein the matrix is selected from the group consisting of a polyester, a nylon, a rayon, and a cotton.

10. The process of claim 1, wherein the matrix is a non-woven, non-absorbent polyester.

11. The process of claim 10, wherein the polyester is a poly(paraphenylene terephthalate).

12. The process of claim 1, wherein the polyhydroxy alcohol is present in a concentration of about 10%.

13. A device for separating plasma from a whole blood sample, comprising a permeable non-glass fiber matrix containing (1) a $C_3$ to $C_{20}$ polyhydroxy alcohol capable of clumping red blood cells and (2) a polycationic polymer, said matrix being porous to red blood cells in the absence of said polyhydroxy alcohol, said matrix further having a first surface and a second surface which are on opposite sides of said matrix, wherein the whole blood sample vertically flows from said first surface toward said second surface and wherein plasma separated from a whole blood sample becomes available at said second surface.

14. The device of claim 13, wherein the polycationic polymer is hexadimethrine bromide.

15. The device of claim 13, wherein the matrix is supported by a permeable filter material.

16. The device of claim 15, wherein the permeable filter material is a reagent layer containing at least one chemical reagent for determining the presence of an analyte in the plasma.

17. The device of claim 15, wherein the permeable filter material is selected from the group consisting of a nylon, a cellulose acetate, a polysulfone, a synthetic fiber, and a polycarbonate.

18. The device of claim 13, wherein the polyhydroxy alcohol is impregnated in the matrix.

19. The device of claim 13, wherein the matrix is selected from the group consisting of a polyester, a nylon, a rayon, and a cotton.

20. The device of claim 13, wherein the matrix is a non-woven, non-absorbent polyester.

21. The device of claim 20, wherein the polyester is a poly(paraphenylene terephthalate).

22. The device of claim 13, wherein the polyhydroxy alcohol is present in a concentration of about 10%.

23. A device for separating plasma from a whole blood sample, comprising:

(a) a non-woven, non-absorbent polyester matrix impregnated with mannitol and hexadimethrine bromide, said matrix being porous to red blood cells in the absence of said mannitol and said matrix further having a first surface and a second surface which are on opposite sides of said matrix, wherein the whole blood sample vertically flows from said first surface toward said second surface and wherein plasma separated from the whole blood sample becomes available at said second surface; and (b) a nylon membrane supporting said matrix.

24. The device of claim 23, wherein mannitol is present in a concentration of about 10%.

25. A process for separating plasma from a whole blood sample, comprising:

(a) applying the whole blood sample to a first surface of a permeable non-glass fiber matrix containing (1) a $C_3$ to $C_{20}$ polyhydroxy alcohol capable of clumping red blood cells and (2) a polycationic polymer, said matrix being porous to red blood cells in the absence of said polyhydroxy alcohol;

(b) flowing said whole blood sample under conditions which allow said sample to flow directionally toward a second surface of said matrix; and (c) receiving plasma separated from said whole blood sample at said second surface.

26. The process of claim 25, wherein the polyhydroxy alcohol is mannitol and further wherein the polycationic polymer is hexadimethrine bromide.

27. The process of claim 25, wherein the polyhydroxy alcohol is present in a concentration of about 10%.

28. A device for separating plasma from a whole blood sample, comprising a permeable non-glass fiber matrix containing (1) a $C_3$ to $C_{20}$ polyhydroxy alcohol capable of clumping red blood cells and (2) a polycationic polymer, said matrix being porous to red blood cells in the absence of said polyhydroxy alcohol, said matrix further having a first surface and a second surface, wherein the whole blood sample is applied to said first surface and flows directionally toward said second surface and further wherein plasma separated from a whole blood sample becomes available at said second surface.

29. The device of claim 28, wherein the polyhydroxy alcohol is mannitol and further wherein the polycationic polymer is hexadimethrine bromide.

30. The process of claim 28, wherein the polyhydroxy alcohol is present in a concentration of about 10%.

* * * * *

UNITED STATES PATENT AND TRADEMARK OFFICE
CERTIFICATE OF CORRECTION

PATENT NO. : 5,725,774
DATED : Mar. 10, 1998
INVENTOR(S) : Gebhard Neyer

It is certified that error appears in the above-identified patent and that said Letters Patent is hereby corrected as shown below:

In column 11, line 33, please delete "0.85 p/n" and replace therefor with --0.85 µm--.

Signed and Sealed this

Seventeenth Day of April, 2001

*Attest:*

NICHOLAS P. GODICI

*Attesting Officer*  Acting Director of the United States Patent and Trademark Office